United States Patent
Crosby et al.

(10) Patent No.: US 6,362,376 B1
(45) Date of Patent: Mar. 26, 2002

(54) PROCESS FOR THE PREPARATION OF 2-HYDROXYALKYL HALOPHENONES

(75) Inventors: John Crosby, Macclesfield; Kevin Douglas Bailey, Huddersfield; Michael John Monteith, Longfield, all of (GB)

(73) Assignee: Avecia Limited, Blackley (GB)

( * ) Notice: Subject to any disclaimer, the term of this patent is extended or adjusted under 35 U.S.C. 154(b) by 0 days.

(21) Appl. No.: 09/923,956

(22) Filed: Aug. 8, 2001

Related U.S. Application Data

(62) Division of application No. 09/673,509, filed as application No. PCT/GB99/01082 on Apr. 8, 1999.

(30) Foreign Application Priority Data

Apr. 18, 1998 (GB) ............................................. 9808447

(51) Int. Cl.$^7$ ..................... C07C 49/163; C07C 49/215; C07C 49/233
(52) U.S. Cl. ...................... 568/325; 568/327; 568/332
(58) Field of Search ................................. 568/325, 327, 568/332

(56) References Cited

U.S. PATENT DOCUMENTS

| | | | |
|---|---|---|---|
| 4,172,097 A | | 10/1979 | Smith et al. |
| 4,530,844 A | * | 7/1985 | Smerbeck et al. |
| 4,563,454 A | | 1/1986 | Kohda et al. |
| 5,629,460 A | | 5/1997 | Thenappan et al. |

FOREIGN PATENT DOCUMENTS

| EP | 0687 672 | 12/1995 |
|---|---|---|
| WO | WO 96/25410 | 8/1996 |

OTHER PUBLICATIONS

Konosu, Toshiyuki et al.: "Triazole antifungals. III. Stereo-controlled synthesis of an optically active triazolylmethyloxirane precursor to antifungal oxazolidine derivatives" Chem. Pharm. Bull. (1991), 39(9), 2241–6, XP002111184, p. 2241, left–hand column, line 33–36; chart 3; p. 2243, right–hand column, lines 10–40.

Database WP1, Section on Ch, Week 9444, Derwent Publications Ltd., London, GB; Class B03, AN 94–354725 XP002111185 & JP 06 279419 A (Tokyo Tanabe Co), Oct. 4, 1994, abstract.

* cited by examiner

*Primary Examiner*—Sreeni Padmanabhan
*Assistant Examiner*—Sikarl A. Witherspoon
(74) *Attorney, Agent, or Firm*—Pillsbury Winthrop LLP

(57) ABSTRACT

2-Benzyloxyalkyl halophenones of the formula (3):

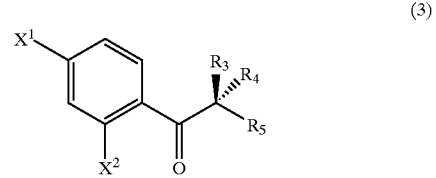

(3)

wherein $X^1$ and $X^2$ are each independently H, Cl or F, provided that at least one of $X^1$ and $X^2$ is Cl or F; one of $R^3$ and $R^4$ is H and the other is optionally substituted benzyloxy; and $R_5$ is an unsubstituted alkyl, preferably a $C_{1-6}$ alkyl group. The compounds are useful as intermediates for preparing 2-hydroxyalkyl halophenones.

5 Claims, No Drawings

PROCESS FOR THE PREPARATION OF 2-HYDROXYALKYL HALOPHENONES

This is a Divisional of National Application Ser. No. 09/673,509 filed Nov. 29, 2000. International Application No. PCT/GB99/01082 filed Apr. 8, 1999 which designated the U.S.

This invention relates to processes for the preparation of certain chiral compounds and to novel compounds used in the processes.

1-(2,4-dihalophenyl)-2-hydroxy-1-propanones are key intermediates for the synthesis of a variety of pharmaceuticals and agrochemicals, particularly antifungal compounds and medicines used in the treatment of AIDS. For example Sch 42427/SM9164 and ER-30346 are made from these intermediates.

The chiral 2-hydroxy group in these compounds. has been prepared by chiral α-hydroxylation of the corresponding 2',4'-difluoropropiophenone. One such method is described in Tetrahedron Letters, Vol 37, No. 45, pp8117–8120 (1996). An alternative method involves the regioselective ring opening of a 2',4'-fluorophenyl propylene oxide, as described in Tetrahedron Letters, Vol 35, No. 45, pp8299–8302 (1994). We have now devised a process for preparing 2,4'-dihalo-2-hydroxypropiophenones with good enantiomeric purity from readily available L- or D-2-chloropropionic acid.

According to one aspect of the present invention there is provided a process for the preparation of a compound of Formula (1):

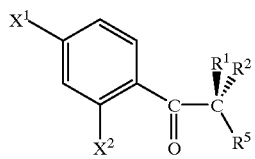
(1)

wherein:
$X^1$ and $X^2$ are each independently H, Cl or F, provided that at least one of $X^1$ and $X^2$ is Cl or F;
one of $R^1$ and $R^2$ is H and the other is OH; and
$R^5$ is an unsubstituted alkyl, preferably a $C_{1-6}$ alkyl, group
comprising the steps:
(a) condensing a 2-chloroalkanoic acid with an optionally substituted benzyl alcohol to form a 2-(optionally substituted benzyloxy) alkanoic acid;
(b) converting the product from step (a) to the corresponding acid chloride; then either:
(c) reacting the product of step (b) with a compound of the Formula (2) in the presence of a source of copper (I) to give a compound of Formula (3) wherein one of $R^3$ and $R^4$ is H and the other is optionally substituted benzyloxy;

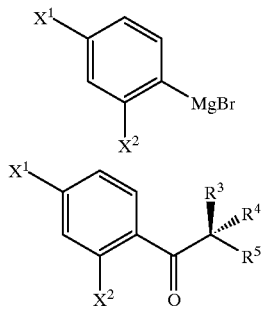

(2)

(3)

or (d) reacting the product of step (b) with a compound of Formula (4):

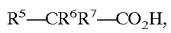
A————NH————B wherein A and B independently represent substituted alkyl, alkoxy, aryl or oxyaryl groups, or are linked to form a heterocyclic ring to form an amide, and then reacting the amide with a compound of Formula (2) to give a compound of Formula (3); and (e) removing the optionally substituted benzyl group from the compound of Formula (3) by hydrogenation, thereby giving the compound of Formula (1).

The process steps a) to d) above for the production of a compound of Formula (3) form another aspect of the present invention.

In step (a) the reaction of the 2-chloroalkanoic acid with an optionally substituted benzyl alcohol proceeds with an inversion of configuration. Accordingly, the choice of which enantiomer of the 2-chloroalkanoic acid will be made on the basis of the desired configuration of the desired compound of Formula (1) or Formula (3). 2-chloroalkanoic acids which can be employed in the present invention have the general formula:

$R^5$—$CR^6R^7$—$CO_2H$, wherein $R^5$ is an alkyl group, preferably a $C_{1-6}$ alkyl group, and most preferably a methyl group, and one of $R^6$ or $R^7$ is Cl, the other being H. The most preferred 2-chloroalkanoic acids are L- and D-2-chloropropionic acid.

The optionally substituted benzyl alcohol is preferably benzyl alcohol or a benzyl alcohol having from 1 to 5 substituents, often selected from the group consisting of halo, preferably F, Cl or Br, nitro; $C_{1-4}$-alkyl, preferably methyl or ethyl; $C_{1-4}$-alkoxy, preferably methoxy or ethoxy; carboxy; sulpho and amino. Benzyl alcohol is most preferred.

The condensation in step (a) is preferably performed in the presence of a strong base, preferably an inorganic base. Examples of suitable organic bases include alkyl lithium salts such as butyl lithium, and alkali metal, especially lithium, alkylamide salts such as lithium diisopropylamide. Examples of suitable inorganic bases include alkali metals, especially lithium, sodium and potassium metal, alkali metal hydrides such as lithium, sodium or potassium hydride, alkali metal hydroxides, carbonates and bicarbonates, especially sodium hydroxide, potassium hydroxide and mixtures thereof.

The condensation of step (a) is preferably performed at an elevated temperature, more preferably 30° C. to 150° C., especially 40° C. to 120° C.

Condensation step (a) can be performed in the presence of an organic solvent which is unreactive towards the reagents employed. Examples of suitable solvents include halocarbons, especially chlorocarbons such as dichloromethane, chloroform, dichloroethane, chlorobenzene, and ethers, particularly $C_{1-6}$ alkylethers such as t-butyl methyl ether and tetrahydrofuran. It is preferred that the benzyl alcohol serves as its own solvent, and in many embodiments, a molar excess of benzyl alcohol over the chloropropionic acid is employed, such as a mole ratio of benzyl alcohol to 2-chloroalkanoic acid of from 2:1 to 15:1, and commonly from 5:1 to 10:1.

Conversion of the product of step (a) to the corresponding acid chloride (i.e. —COCl) is preferably performed using oxalyl chloride, thionyl chloride, or a phosphorus halide, such as $PCl_3$ or $PCl_5$. Elevated temperatures are preferred, especially 30° C. to 110° C., more preferably 35° C. to 90°

C. The reaction is commonly carried out neat, but an organic solvent which is unreactive towards the reagents may be employed. Examples of suitable solvents include halocarbons, especially chlorocarbons such as dichloromethane, chloroform, dichloroethane, chlorobenzene; ethers, particularly $C_{1-6}$ alkylethers such as t-butyl methyl ether and tetrahydrofuran; and aromatic solvents such as toluene.

The source of copper (I) used in step (c) is preferably a Cu (I) salt, such as $CuNO_3$, CuCN or a copper (I) halide, especially CuCl, CuBr or CuI. The amount of copper (I) source used is preferably between 80 and 200 mole % relative to the number of moles of the acid chloride product of step (b), more preferably from 85 to 150 mole %, especially 90 to 140 mole %.

Step (c) is commonly carried out in the presence of an organic solvent which is unreactive towards the reagents is commonly employed. Examples of suitable organic solvents include ethers, particularly $C_{1-6}$ alkylethers such as t-butyl methyl ether and tetrahydrofuran; and aromatic solvents such as toluene. The reaction temperature of step (c) is commonly in the range of from −78° C. to 30° C., and preferably from −40° C. to 0° C.

The compound of Formula (2) is commonly prepared by reacting the appropriately substituted phenyl bromide with magnesium metal in the presence of a suitable solvent, often the solvent employed in step (c). Preferably, a stoichiometric ratio or moderate molar excess of phenyl bromide to magnesium is employed, often a molar ratio of from 1:1 to 2:1, and advantageously from 1.25:1 to 1.75:1. The preparation often takes place at a temperature of from ambient temperature (20–25° C.) to about 35° C. It will be recognised that the preparation of compounds of Formula (2) can be exothermic, and so appropriate cooling is advantageously provided to control such exotherms.

In the amine compound of Formula (4) employed in step (d), when A or B represents an alkyl or alkoxy group, it is preferably a $C_{1-4}$ alkyl or alkoxy group, and particularly a methyl or methoxy group. When A or B represents an aryl or aryloxy group, it is preferably a phenyl or phenoxy group. When A and B are linked to form a ring, the ring preferably contains from 5 to 8 members, and 1, 2 or 3 heteroatoms. In addition to the amine nitrogen, other heteroatoms, especially oxygen may be present in the ring. Examples of preferred amines include morpholine, pyrrolidine and N-methoxy-N-methylamine. The amine can be employed as a free amine or in the form of a salt, especially a hydrochloride salt. The mole ratio of amine to acid chloride is commonly from 1:1 to 2:1. Step (d) is commonly carried out in the presence of an organic solvent which is unreactive towards the reagents is commonly employed. Advantageously, the solvent employed is substantially water insoluble. Examples of suitable organic solvents include halocarbons, especially chlorocarbons such as dichloromethane, chloroform, dichloroethane, chlorobenzene; ethers, particularly $C_{1-6}$ alkylethers such as t-butyl methyl ether and tetrahydrofuran; and aromatic solvents such as toluene. Step (d) is commonly carried out a temperature of from 0 to 30° C.

In step (e) the optionally substituted benzyl group can be removed by methods known in the art, and is preferably removed from the compound of Formula (3) by hydrogenation using a transition metal catalyst and hydrogen gas. Preferred transition metal catalysts are in group VIII of the periodic table, more preferably palladium, nickel and platinum, and especially palladium on carbon, often on activated carbon. Loadings of metal on carbon are commonly in the range of from 1 to 20% w/w, and preferably from about 5% to about 10% w/w. Degussa-type palladium on activated carbon has been found to be advantageous in certain embodiments of the present invention. Solvents that can be employed in the removal of the optionally substituted benzyl group by hydrogenation include alcohols, particularly $C_{1-4}$ alkyl alcohols; esters, particularly esters of $C_{1-4}$ carboxylic acids with $C_{1-4}$ alcohols, preferably ethyl acetate; and aromatic solvents such as toluene. Step (e) is commonly carried out a temperature of from about 10 to 30° C., commonly at ambient temperature, such as 15 to 25° C.

The compounds of Formula (3) are valuable intermediates in their own right and generally have useful crystalline properties. This enables the compound of Formula (3) to be crystallised thereby greatly enhancing the purity, both chemical and particularly optical, of the desired compound of Formula (1) and downstream pharmaceutical and agrochemical products. Furthermore, the compounds of Formula (3) are much more stable than the corresponding free hydroxy compounds and are therefore more readily transportable. They can also be stored for extended periods, with conversion to the corresponding free hydroxy compound being necessary only immediately prior to its use. Thus in a preferred embodiment the product of step (c) or (d) is purified by recrystallisation before step (e) is performed. Recrystallisation is preferably performed in an organic solvent, more preferably in hydrocarbon solvent, especially a linear of branched aliphatic hydrocarbon, such as n- or iso-pentane, n- or iso-hexane, cyclohexane and petroleum fractions.

Accordingly the present invention also provides compounds of Formula (3) wherein $X^1$ and $X^2$ are each independently H, Cl or F, provided that at least one of $X^1$ and $X^2$ is Cl or F; one of $R^3$ and $R^4$ is H and the other is optionally substituted benzyloxy; and $R^5$ is an unsubstituted alkyl, preferably a $C^{1-6}$ alkyl, group. Preferably, both of $X^1$ and $X^2$ represent Cl or F, and especially both are F. The benzyloxy group is often unsubstituted. $R^5$ is most commonly a methyl group.

The process for the production of compounds of Formula (3) preferably comprises the further step of purifying the compound of Formula (3) by recrystallisation from an organic solvent, more preferably from one of the organic solvents mentioned above in the recrystallisation process for purifying the products of steps (c) and (d).

The invention is further illustrated without limitation by the following examples in which all parts and percentages are by weight unless specified otherwise and %Str. is per cent strength.

EXAMPLE 1

Stage (i)

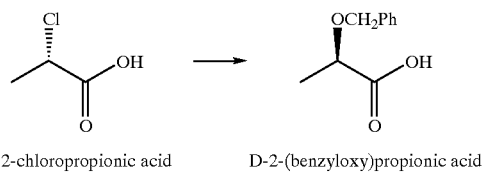

L-2-chloropropionic acid    D-2-(benzyloxy)propionic acid

Sodium metal (34.5 g, 1.5 moles) was added in small portions with cooling to benzyl alcohol (440 g, 4.1 moles). The mixture was stirred at 80–90° C. for 2 hours, cooled to 55° C. and L-2-chloropropionic acid (68.6 g, 0.63 moles) was added over about 1 hour. The mixture was stirred at 55° C. until gas chromatography indicated that the condensation was complete (about 2 hours). Water (350 ml) was added and the pH was adjusted to 6.5 using concentrated HCl. Tert-butyl methyl ether ("TBME", 250 ml) was added, the mixture was stirred for 5 minutes and then allowed to settle. Water (150 ml) and TBME (250 ml) were added. The aqueous layer was removed and washed with TBME (500 ml and 3×250 ml washings). The washed, aqueous layer was then acidified to pH 1.5 using concentrated HCl to liberate the desired product and the product was extracted with TBME (2×250 ml). The combined 500 ml of TBME was washed with water (200 ml) and the solvent removed in vacuo at 50° C., 300 mmHg pressure to give the desired D-2-(benzyloxy)propionic acid (96.1 g, 84%).

Stage (ii)

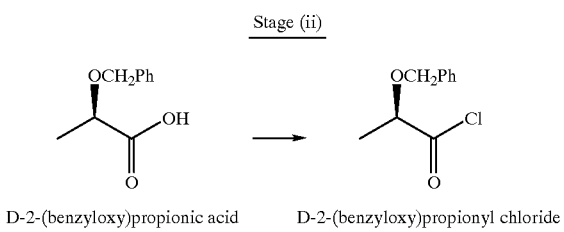

D-2-(benzyloxy)propionic acid          D-2-(benzyloxy)propionyl chloride

Oxalyl chloride (112 g, 0.88 moles) was added dropwise at 20° C. to the product of stage (a) (102.86 g, 0.57 moles). The temperature rose rapidly to 35° C. When the exotherm had ceased the mixture was heated to 45–50° C. and the remainder of the oxalyl chloride was added at this temperature over 45 minutes. After stirring the mixture at 50–55° C. for 1.5 hours the temperature was increased to 105° C. with a nitrogen sparge to remove any residual oxalyl chloride. The desired D-2-(benzyloxy)propionyl chloride was obtained as an oil (109.7 g, 94.9%).

Stage (iii)

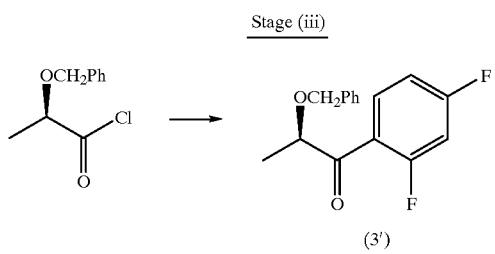

(3')

An aliquot (ca. 5–10 ml) of a solution of 2,4-Difluorobromobenzene (98.4 g, 0.5 moles) in tetrahydrofuran ("THF") (75ml) was added to a stirred mixture of Mg turnings (12.25 g, 0.51 moles) in THF (340 ml) at ambient temperature. After 35 minutes stirring at ambient temperature the reaction initiated. When the temperature reached 27° C. an ice/water bath was used to cool the reaction mixture but the temperature still reached 50° C. before the exotherm subsided. The mixture was cooled to 25° C. and the remainder of the solution of bromodifluorobenzene/THF solution added to the Mg/THF solution with cooling over 0.5 h at 20–30° C. The mixture was stirred for a further 1.5 hours, CuCl (56.5 g, 0.57 moles, dried at 110° C. for 17 hours) was added over 20 minutes at 20–30° C. (ice bath cooling) and the mixture stirred for a further 1.5 hours at 20–30° C. The mixture was cooled to −30° C. and the acid chloride added over 20 minutes at −25 to 30° C. The mixture was then allowed to warm to room temperature and monitored by GC. After stirring overnight (17 hours), 5% GC area of the acid chloride still remained.

200 ml of 18% HCl was added, keeping the temperature below 30° C. This acid dissolved almost all the solids apart from some residual CuCl. TBME (250 ml) was added and the mixture stirred for 10 mins. The two dark phases separated well and the aqueous phase was removed (120 ml). To the organic was added further TBME (100 ml) and the organic washed with 18% HCl (100 ml). Water (100 ml) was added and an emulsion was produced. The mixture was shaken and allowed to settle. A good separation then resulted. The aqueous was removed (240 ml). The organic extract was sequentially washed with 3×18% HCl (200 ml) (in each case more than 200 ml aqueous was removed) washes and then a water wash (200 ml). The water wash resulted in a precipitate in the organic phase. To the mixture (containing the water wash) was added conc. HCl (50 ml). The mixture was shaken then settled to give 2 phases. The aqueous was removed and the organic diluted with further TBME (250 ml) was washed with water (150 ml). An emulsion resulted and conc. HCl (50 ml) was added. The emulsion cleared to give two phases. The aqueous was removed and the organic washed with water (2×500 ml). Some solids were apparent in the aqueous phase and these were removed with the aqueous washings. The organic was then washed with 9% HCl (200 ml), water (200 ml), 5% sodium carbonate (200 ml) and water (200 ml). The solvent was removed in vacuo at 60° C./20 mmHg to give the above product (3') as a brown oil.

Stage (iv)

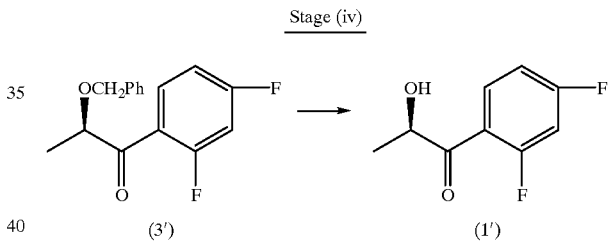

(3')          (1')

Hydrogen gas was bubbled through a solution of (3') (2 g, 0.0072 moles) in methanol (50 ml) in the presence of a catalyst (5% Pd on carbon, 0.2 g at 50% water content, Degussa Type E101). When gas chromatography showed the reaction had gone to completion the catalyst was removed by filtration under nitrogen and methanol removed in vacuo to give (1') as an oil (1.3 g, 95%).

EXAMPLE 2

| (i) Preparation of morpholine amide | | | | | | | |
|---|---|---|---|---|---|---|---|
| Material | Source | % Str. | Weight (g) | 100% Wt. (g) | MWt. | Moles | Mole ratio |
| D-2-benzyl-oxypropionyl chloride | | 92 | 41.71 | 38.37 | 198.5 | 0.193 | 1 |
| Morpholine | Aldrich | 99+ | 33.96 | 33.62 | 87.1 | 0.386 | 2 |
| Dichloro-methane | Fisons | | 88 + 88 ml | | | | |
| Water | | | 100 ml + 100 ml | | | | |

D-2-benzyloxypropionyl chloride, prepared by the method of Example 1, stages (i) and (ii), was dissolved in dichloromethane (88 ml) and cooled (0–10° C.). Morpholine was dissolved in dichloromethane (88 ml) and added to the solution of D-2-benzyloxypropionyl chloride in dichloromethane keeping the temperature between 0–10° C. The addition took 25 minutes and a white precipitate formed. The reaction was stirred for two hours at ca. 25° C. Water was added and the lower organic layer was recovered and then washed with water. The organic phase was concentrated to give an oil (48.5 g, 96% yield).

The morpholine amide was dissolved in the THF. The solution of Grignard was added over 20 minutes at 20–30° C. (required slight cooling). The reaction was stirred for 1 hour and sampled by GC. The % conversion was used to calculate an additional charge of Grignard. The additional Grignard was added and the reaction was stirred for 1 hour. The reaction mixture was poured into aq. 1N HCl at 20–30° C. (required slight cooling). The mixture was extracted with ethyl acetate. The upper organic layer was recovered and concentrated to give an orange oil (22.8 g, 99% yield).

(ii) Preparation of stock solution of Grignard: 2,4-difluorophenylmagnesium bromide

| Material | Source | % Str. | Weight (g) | 100% Wt. (g) | MWt. | Moles | Mole ratio |
|---|---|---|---|---|---|---|---|
| Mg turnings | Aldrich | 98 | 2.78 | 2.72 | 24 | 0.113 | 1.05 |
| 2,4-difluorobromobenzene | Aldrich | 99+ | 21.27 | 20.8 | 193 | 0.108 | 1 |
| THF | Fisons | | 66 ml | | | | |

The magnesium was added to the minimum amount of THF (10 ml) required to cover the metal. The 2,4-difluorobromobenzene was dissolved in the balance of the THF (56 ml). Approximately 5 ml of this solution was charged to the slurry of Mg/THF. Initiation occurred after 5 minutes as seen by an exotherm which reached 50° C. before cooling was applied to return the temperature to 30° C. The balance of the 2,4-difluorobromobenzene solution was added over 30 minutes keeping the temperature at 25–35° C. The mixture was stirred for 2–2.5 hours at 30–35° C. The total volume was about 66 ml making the solution ~1.6M assuming complete reaction.

(iv) Recrystallisation

The crude product from step (iii) was dissolved in hexane (10 ml) and cooled (0–50° C.). The solution was stirred for 2–3 hours. The mixture was seeded after 1 hour. The material crystallised as a white/yellow solid which was filtered through pre-cooled apparatus and washed with cold hexane (5 ml) to give 9.4 g at 99% Str.—50% recovery based on % Str.

EXAMPLE 3

(iii) Reaction of morpholine amide with Grignard

| Material | Source | % Str. | Weight (g) | 100% Wt. (g) | MWt. | Moles | Mole ratio |
|---|---|---|---|---|---|---|---|
| Morpholine amide | Ex. 2(i) | 95 | 20 | 19 | 249 | 0.076 | 1 |
| 2,4-difluoro phenyl magnesium bromide | Ex. 2(ii) | | 55 ml + extra based on GC | | | 0.088 | 1.15 + extra as required |
| THF | Fisons | | 50 ml | | | | |
| 1N HCl | Rimon | | 200 ml | | | 0.2 | 2.63 |
| Ethyl acetate | Fisons | | 50 ml | | | | |

(i) Preparation of Weinreb amide

| Material | Source | % Str. | Weight (g) | 100% Wt. (g) | MWt. | Moles | Mole ratio |
|---|---|---|---|---|---|---|---|
| D-2-benzyl-oxypropionyl chloride | | 93.5 | 21.21 | 19.83 | 198.5 | 0.1 | 1 |
| N,O-Dimethyl hydroxyl amine,HCl | Aldrich | 98 | 9.98 | 9.78 | 97.55 | 0.1 | 1 |

-continued

(i) Preparation of Weinreb amide

| Material | Source | % Str. | Weight (g) | 100% Wt. (g) | MWt. | Moles | Mole ratio |
|---|---|---|---|---|---|---|---|
| Pyridine | Aldrich | 99%+ | 15.8 | 15.64 | 79.1 | 0.198 | 2 |
| Dichloromethane | Fisons | | 89 + 16 ml | | | | |
| 1N HCl | Rimon | | 200 ml | | | 0.2 | 2 |
| Ethyl acetate | Fisons | | 100 ml | | | | |

A solution of pyridine in dichloromethane (16 ml) was added dropwise to a suspension of N,O-dimethylhydroxylamine hydrochloride and D-2-benzyloxypropionyl chloride (prepared by the method of Example 1, stages (i) and (ii)) in dichloromethane (89 ml) at 20–30° C. The mixture was stirred overnight. The solvent was removed and the residue partitioned between 1N HCl and EtOAc. The organic phase was recovered and concentrated to give an oil (22.0 g, 95% yield).

(ii) Preparation of Stock Solution of Grignard: 2,4-difluorophenylmagnesium bromide Prepared by the method above for Example 2(ii)

(iii) Reaction of Weinreb amide with Grignard

| Material | Source | % Str. | Weight (g) | 100% Wt. (g) | MWt. | Moles | Mole ratio |
|---|---|---|---|---|---|---|---|
| Weinreb amide | Ex. 3(i) | 96 | 15 | 14.5 | 223 | 0.065 | 1 |
| 2,4-difluorophenyl magnesium bromide | Ex. 3(ii) | | 45 ml + extra based on GC (2.4 ml) | | | 0.072 | 1.1 + extra as required (0.06) |
| THF | Fisons | | 40 ml | | | | |
| 1N HCl | Rimon | | 200 ml | | | 0.2 | 2.63 |
| Ethyl acetate | Fisons | | 50 ml | | | | |

The Weinreb amide was dissolved in the THF. The solution of Grignard was added over 20 minutes at 20–30° C. (required slight cooling). The reaction was stirred for 30 minutes and sampled by GC. The % conversion was used to calculate an additional charge of Grignard. The additional Grignard was added and the reaction was stirred for 45 minutes. The reaction mixture was poured slowly into aq. 1N HCl at 20–30° C. (required slight cooling). The mixture was extracted with ethyl acetate. The upper organic layer was recovered and concentrated to give an oil 17.4 g, 89% yield.

(iv) Recrystallisation 2 g of the crude product from step (c) was dissolved in hexane (1.5 ml) and cooled (0–5° C.). The solution was stirred for 1.5 hours. The mixture was seeded after 1 hour. The material crystallised as a white/yellow solid which was filtered through pre-cooled apparatus and washed with cold hexane (0.5 ml) to give 1.2 g at 98% Str.—66% recovery based on % Str.

What is claimed is:

1. A compound having the general chemical Formula (3):

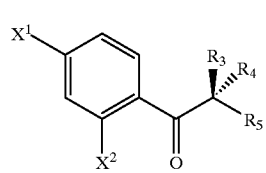

(3)

wherein:
  $X^1$ and $X^2$ are each independently H, Cl or F, provided that at least one of $X^1$ and $X^2$ is Cl or F;
  one of $R^3$ and $R^4$ is H and the other is optionally substituted benzyloxy; and
  $R^5$ is an unsubstituted alkyl.

2. A compound according to claim 1, wherein $X^1$ and $X^2$ are both F.

3. A compound according to either of claim 1 or 2, wherein $R^5$ represents a methyl group.

4. A compound according to claim 1 wherein $X^1$ and $X^2$ are F, $R^3$ is $OCH_2Ph$, $R^4$ is H and $R^5$ is Me.

5. A compound according to claim 1 wherein $X^1$ and $X^2$ are F, $R^3$ is H, $R^4$ is $OCH_2Ph$ and $R^5$ is Me.

* * * * *